(12) United States Patent
Thompson et al.

(10) Patent No.: US 11,648,026 B2
(45) Date of Patent: May 16, 2023

(54) DEVICES, SYSTEMS, AND METHODS FOR COOLING A SURGICAL INSTRUMENT

(71) Applicant: Covidien LP, Mansfield, MA (US)

(72) Inventors: James E. Thompson, Frederick, CO (US); Robert B. Smith, Loveland, CO (US); Daniel A. Friedrichs, Aurora, CO (US)

(73) Assignee: Covidien LP, Mansfield, MA (US)

( * ) Notice: Subject to any disclaimer, the term of this patent is extended or adjusted under 35 U.S.C. 154(b) by 468 days.

(21) Appl. No.: 16/840,775

(22) Filed: Apr. 6, 2020

(65) Prior Publication Data

US 2020/0229843 A1 Jul. 23, 2020

Related U.S. Application Data

(62) Division of application No. 15/155,953, filed on May 16, 2016, now Pat. No. 10,646,246.

(51) Int. Cl.
*A61B 17/32* (2006.01)
*A61B 18/00* (2006.01)
*A61B 17/00* (2006.01)

(52) U.S. Cl.
CPC .......... *A61B 17/320092* (2013.01); *A61B 17/320068* (2013.01); *A61B 2017/0003* (2013.01);
(Continued)

(58) Field of Classification Search
CPC .... A61B 17/320092; A61B 17/320068; A61B 2017/00084
See application file for complete search history.

(56) References Cited

U.S. PATENT DOCUMENTS 5,383,876 A 1/1995 Nardella
5,391,144 A 2/1995 Sakurai et al.
(Continued)

FOREIGN PATENT DOCUMENTS

CN 201939898 U 8/2011
EP 00514810 A1 11/1992
EP 2572660 A2 3/2013

OTHER PUBLICATIONS

Extended European Search Report issued in corresponding European Patent Application No. 17170970.2 dated Oct. 18, 2017.
(Continued)

*Primary Examiner* — Toan M Le
(74) *Attorney, Agent, or Firm* — Carter, DeLuca & Farrell LLP

(57) ABSTRACT

A surgical system includes a surgical instrument and a cooling module. The cooling module includes a fluid reservoir retaining a conductive cooling fluid, a pump configured to pump the conductive cooling fluid along a flowpath, first and second electrodes disposed at first and second positions along the flowpath and configured to sense an electrical property of the conductive cooling fluid at the first and second positions, and a controller configured to determine an impedance of the conductive cooling fluid between the first and second positions based upon the sensed electrical properties of the first and second electrodes. A method for cooling a surgical instrument includes detecting an electrical property of a conductive cooling fluid at first and second positions along a flowpath and determining an impedance of the conductive cooling fluid between the first and second positions based upon the detected electrical properties at the first and second positions.

9 Claims, 11 Drawing Sheets

(52) U.S. Cl.
CPC ............... *A61B 2017/00084* (2013.01); *A61B 2017/320094* (2017.08); *A61B 2018/00023* (2013.01)

(56) References Cited

U.S. PATENT DOCUMENTS

| | | | |
|---|---|---|---|
| 6,142,992 | A | 11/2000 | Cheng et al. |
| 6,206,876 | B1 | 3/2001 | Levine et al. |
| 6,379,371 | B1 | 4/2002 | Novak et al. |
| 6,633,234 | B2 | 10/2003 | Wiener et al. |
| 6,764,487 | B2 | 7/2004 | Mulier et al. |
| 7,074,219 | B2 | 7/2006 | Levine et al. |
| 7,404,816 | B2 | 7/2008 | Abboud et al. |
| 7,530,986 | B2 | 5/2009 | Beaupre et al. |
| 8,628,534 | B2 | 1/2014 | Jones et al. |
| 8,727,983 | B2 | 5/2014 | Kinnison |
| 8,974,478 | B2 | 3/2015 | Ross et al. |
| 9,044,261 | B2 | 6/2015 | Houser |
| 9,113,930 | B2 | 8/2015 | Reid, Jr. |
| 9,113,943 | B2 | 8/2015 | Ross et al. |
| 2003/0181904 | A1 | 9/2003 | Levine et al. |
| 2004/0199226 | A1* | 10/2004 | Shadduck ............... A61B 18/04 977/900 |
| 2005/0119647 | A1 | 6/2005 | He et al. |
| 2005/0209578 | A1 | 9/2005 | Christian Evans et al. |
| 2008/0015563 | A1 | 1/2008 | Hoey et al. |
| 2008/0154252 | A1 | 6/2008 | Torchia et al. |
| 2009/0287201 | A1 | 11/2009 | Lalonde et al. |
| 2010/0174169 | A1 | 7/2010 | Razavi |
| 2010/0228162 | A1 | 9/2010 | Sliwa et al. |
| 2011/0077635 | A1 | 3/2011 | Bonn |
| 2014/0303611 | A1 | 10/2014 | Shadduck et al. |
| 2015/0073457 | A1 | 3/2015 | Stoddard et al. |
| 2015/0073458 | A1 | 3/2015 | Stoddard et al. |
| 2015/0165240 | A1 | 6/2015 | Stoddard et al. |

OTHER PUBLICATIONS

European Examination Report (Communication Pursuant to Article 94(3) EPC) issued in corresponding European Application No. 17 170 970.2 dated Jul. 16, 2021, 5 pages.

\* cited by examiner

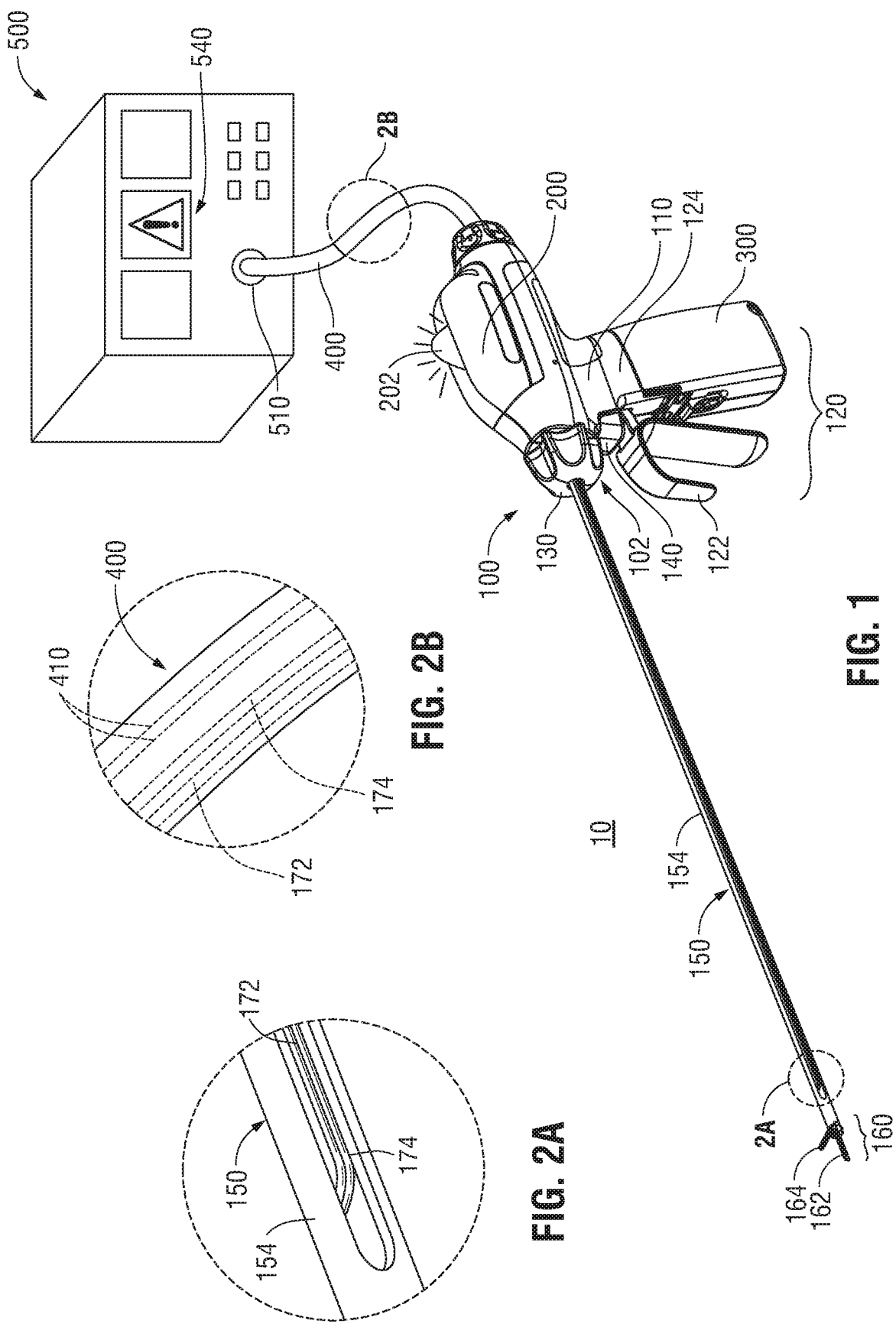

DEVICES, SYSTEMS, AND METHODS FOR COOLING A SURGICAL INSTRUMENT

CROSS REFERENCE TO RELATED APPLICATION

This application is a divisional application of U.S. patent application Ser. No. 15/155,953, filed on May 16, 2016, the entire contents of which are incorporated by reference herein.

FIELD

The present disclosure relates to devices, systems, and methods for cooling a surgical instrument and, in particular, to devices, systems, and methods for cooling a surgical instrument and systems and methods for controlling the same.

BACKGROUND

Energy-based tissue treatment is well known in the art. Various types of energy (e.g., electrical, ultrasonic, microwave, cryogenic, thermal, laser, etc.) are applied to tissue to achieve a desired result. Ultrasonic energy, for example, may be delivered to tissue to treat, e.g., coagulate and/or cut, tissue.

Ultrasonic surgical instruments, for example, typically include a waveguide having a transducer coupled thereto at a proximal end of the waveguide and an end effector disposed at a distal end of the waveguide. The waveguide transmits ultrasonic energy produced by the transducer to the end effector for treating tissue at the end effector. The end effector may include a blade, hook, ball, shears, etc., and/or other features such as one or more jaws for grasping or manipulating tissue. During use, the waveguide and/or end effector of an ultrasonic surgical instrument can reach temperatures greater than 200° C.

It would therefore be desirable to provide devices, systems, and methods for cooling a surgical instrument and controlling cooling of the same.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A surgical system provided in accordance with aspects of the present disclosure includes a surgical instrument defining an input and an output, and a cooling module operably coupled to the input and output of the surgical instrument. The cooling module includes a fluid reservoir retaining a conductive cooling fluid, a pump assembly, first and second electrodes, and a controller. The pump assembly is operably coupled to the fluid reservoir and configured to pump the conductive cooling fluid along a flowpath from the fluid reservoir, into the input of the surgical instrument, through at least a portion of the surgical instrument, out the output of the surgical instrument, and back to the fluid reservoir. The first and second electrodes are disposed at first and second spaced-apart positions along the flowpath and are configured to sense an electrical property of the conductive cooling fluid at the first and second positions. The controller is configured to determine an impedance of the conductive cooling fluid between the first and second positions based upon the sensed electrical properties of the first and second electrodes.

In an aspect of the present disclosure, the surgical instrument includes an ultrasonic waveguide having a blade defined at the distal end thereof. In such aspects, the flowpath may extend at least partially through the blade. The surgical instrument may further include an ultrasonic transducer coupled to the ultrasonic waveguide and configured to energize the blade for treating tissue therewith.

In another aspect of the present disclosure, the surgical system further includes a generator configured to supply energy to the surgical instrument. The generator may be disposed on the surgical instrument or may be spaced-apart therefrom.

In yet another aspect of the present disclosure, the surgical instrument further includes an activation button operably coupled to the generator and including a first activated position and a second activated position for activating the surgical instrument in a first mode and a second mode. In such aspects, the first and second electrodes may be operably coupled to the generator through the activation button.

In still another aspect of the present disclosure, the first position is disposed adjacent a distal end of the surgical instrument and/or the second position is disposed adjacent the cooling module.

In still yet another aspect of the present disclosure, the controller is configured to determine a temperature of the surgical instrument based upon the determined impedance. Additionally or alternatively, the controller is configured to determine whether the flowpath has been properly primed with the conductive cooling fluid based upon the determined impedance. Additionally or alternatively, the controller is configured to at least one of start or stop the pump assembly based upon the determined impedance. Additionally or alternatively, the controller is configured to control the pump assembly based upon the determined impedance. Additionally or alternatively, the controller is configured to determine the presence of at least one of air bubbles, a blockage, or mechanical damage to the surgical instrument based upon the determined impedance.

In another aspect of the present disclosure, the cooling module is disposed on the surgical instrument. Alternatively, the cooling module may be spaced-apart from the surgical instrument.

A method for cooling a surgical instrument provided in accordance with aspects of the present disclosure includes detecting an electrical property of a conductive cooling fluid at a first position along a flowpath from a fluid reservoir, into an input of a surgical instrument, through at least a portion of the surgical instrument, out an output of the surgical instrument, and back to the fluid reservoir. The method further includes detecting an electrical property of the conductive cooling fluid at a second position along the flowpath and determining an impedance of the conductive cooling fluid between the first and second positions based upon the detected electrical properties at the first and second positions.

In an aspect of the present disclosure, the method further includes determining whether the flowpath has been properly primed with the conductive cooling fluid based upon the determined impedance. Additionally or alternatively, the method may further include at least one of initiating or stopping flow of the conductive fluid along the flowpath based upon the determined impedance. Additionally or alternatively, the method may further include determining at least one of air bubbles, a blockage, or mechanical damage to the surgical instrument based upon the determined impedance.

BRIEF DESCRIPTION OF THE DRAWINGS

Various aspects and features of the present disclosure are described hereinbelow with reference to the drawings wherein like numerals designate identical or corresponding elements in each of the several views:

FIG. 1 is a perspective view of a surgical system provided in accordance with the present disclosure including an endoscopic ultrasonic surgical instrument, a cooling module, and a cooling system incorporated therein;

FIG. 2A is an enlarged, perspective view of the area of detail indicated as "2A" in FIG. 1;

FIG. 2B is an enlarged, perspective view of the area of detail indicates as "2B" in FIG. 1;

DETAILED DESCRIPTION

Figure 3:
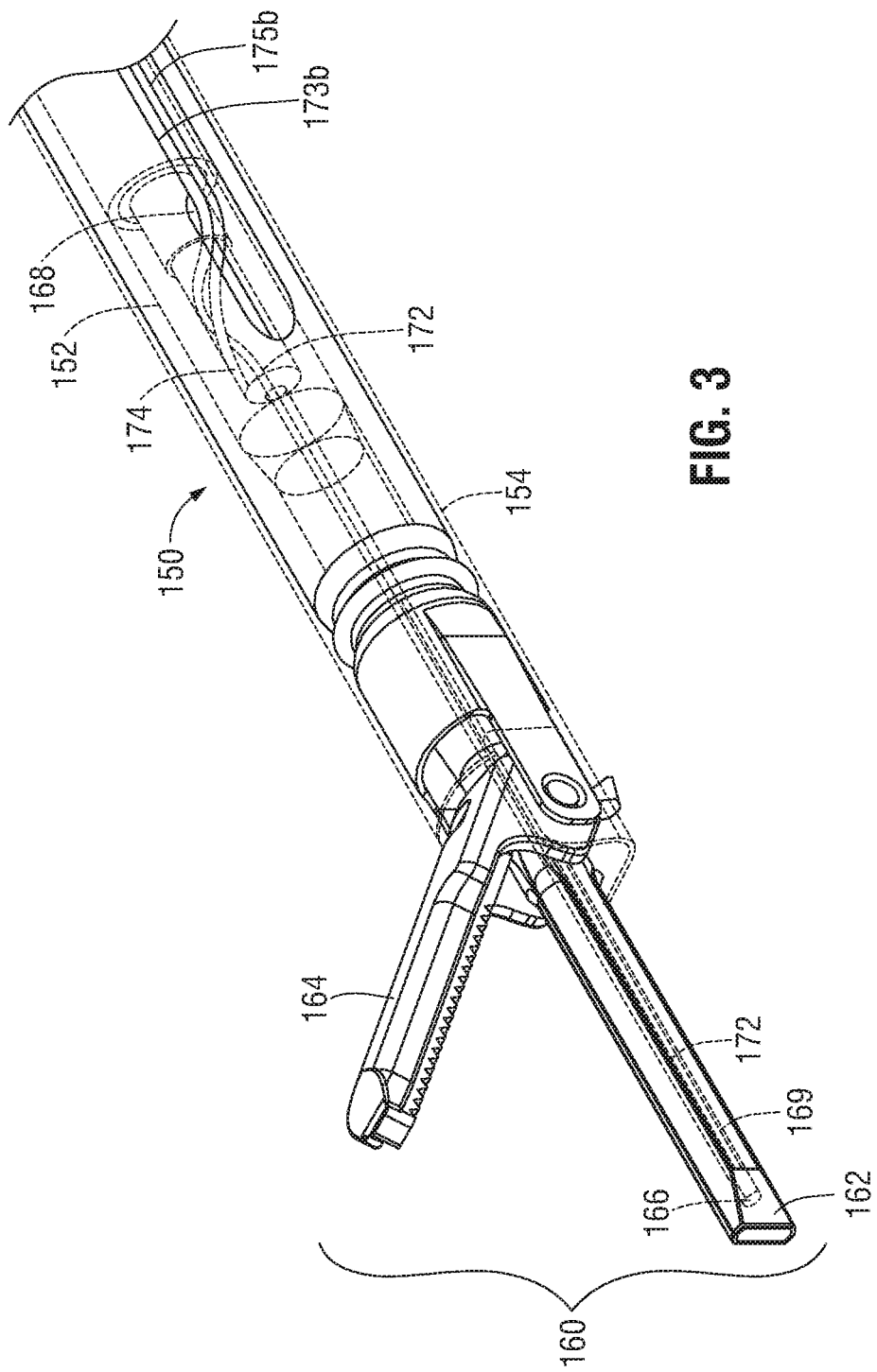
FIG. 3 is an enlarged, perspective view of the distal end of the surgical instrument of FIG. 1.

FIG. 1 depicts a surgical system 10 provided in accordance with the aspects and features of the present disclosure. Surgical system 10 generally includes an endoscopic ultrasonic surgical instrument 100 and a base unit 500 that, together, incorporate a cooling system for cooling a blade 162 of an end effector assembly 160 of endoscopic ultrasonic surgical instrument 100. Although detailed hereinbelow with respect to surgical system 10 and, more particularly, endoscopic ultrasonic surgical instrument 100 and cooling module 500 thereof, the aspects and features of the present disclosure are equally applicable for use with any other suitable surgical system, surgical instrument, and/or cooling module incorporating a cooling system. For example, the aspects and features may be provided for use in connection with a surgical system 20 including an endoscopic ultrasonic surgical instrument 1100 incorporating a cooling module 1500 thereon (see FIG. 5). Further still, another surgical instrument provided in accordance with the present disclosure, open ultrasonic surgical instrument 2100 (FIGS. 6-9), may similarly incorporate the aspects and features of the present disclosure. Obviously, different considerations apply to each particular type of system, instrument, and/or unit; however, the aspects and features of the present disclosure are equally applicable and remain generally consistent with respect to any such system, instrument, and/or unit.

Continuing with reference to FIG. 1, endoscopic ultrasonic surgical instrument 100 generally includes a disposable 102, a transducer and generator assembly ("TAG") 200 including a transducer 210 and a generator 220 (FIG. 4), a battery 300, and a cable 400. Disposable 102 includes a housing 110, a handle assembly 120, a rotating assembly 130, an activation button 140, an elongated body portion 150, and end effector assembly 160. TAG 200 and battery 300 are releasably engagable with housing 110 of disposable 102 and, when engaged therewith, are disposed in electrical communication with one another such that power and/or control signals can be relayed between TAG 200 and battery 300 for operating instrument 100. TAG 200 may further include an indicator 202 disposed thereon, which will be described in greater detail below.

Elongated body portion 150 of disposable 102 of instrument 100 includes a waveguide 152 which extends from housing 110 to end effector assembly 160, an outer tube 154, and an inner tube (not shown). The distal end of waveguide 152 extends distally from outer tube 154 and defines blade 162 of end effector assembly 160, while the proximal end of waveguide 152 is operably coupled to TAG 200. Outer tube 154 is slidably disposed about waveguide 152 and extends between housing 110 and end effector assembly 160. Rotating assembly 130 is rotatably mounted on housing 110 and operably coupled to elongated body portion 150 so as to enable rotation of elongated body portion 150 and end effector assembly 160 relative to housing 110.

End effector assembly 160 is disposed at a distal end of elongated body portion 150 and includes blade 162 and a jaw member 164. Jaw member 164 is pivotable relative to blade 162 between an open position, wherein jaw member 164 is spaced-apart from blade 162, and a closed position, wherein jaw member 164 is approximated relative to blade 162 in juxtaposed alignment therewith for clamping tissue therebetween. Jaw member 164 is operably coupled to the distal end of outer tube 154 and the proximal end of outer tube 154 is operably coupled to movable handle 122 of a handle assembly 120, such that jaw member 164 is movable between the open position and the closed position in response to actuation of movable handle 122 of handle assembly 120 relative to fixed handle portion 124 thereof.

Blade 162 is configured to serve as an active or oscillating ultrasonic member that is selectively activatable to ultrasonically treat tissue grasped between blade 162 and jaw member 164. TAG 200 is configured to convert electrical energy provided by battery 300 into mechanical energy that is transmitted along waveguide 152 to blade 162. More specifically, TAG 200 is configured to convert the electrical energy provided by battery 300 into a high voltage alternating current (AC) waveform that drives the transducer (not shown) of TAG 200. Activation button 140 is disposed on housing 110 of disposable 102 and is electrically coupled between battery 300 and TAG 200. Activation button 140 is selectively activatable in a first position and a second position to supply electrical energy from battery 300 to TAG 200 for operating instrument 100 in a low-power mode of operation and a high-power mode of operation, respectively.

Referring to FIGS. 1-3, cooling inflow and return conduits 172, 174 extend from cooling module 500, through housing 110, and at least partially through outer tube 154 of elongated body portion 150 substantially along the length thereof. Proximal ends 173a, 175a of inflow and return conduits 172, 174, respectively, are operably coupled to cooling module 500, as detailed below (see also FIG. 4).

With particular reference to FIG. 3, distal ends 173b, 175b of inflow and return conduits 172, 174, respectively, extend into waveguide 152. More specifically, a lumen 166 is formed within waveguide 152 that extends through a portion of waveguide 152 including substantially along the length of blade 162 of waveguide. Lumen 166 defines a closed distal end. Conduits 172, 174 enter lumen 166 through an opening 168 defined within waveguide 152 and disposed in communication with lumen 166. A seal (not shown) disposed within opening 168 and around inflow and return conduits 172, 174 is provided to inhibit the escape of fluid therefrom. Inflow conduit 172 is disposed within and extends distally through lumen 166. Return conduit 174 is disposed within the proximal end of lumen 166, although the above-detailed configuration of inflow and return conduits 172, 174 may be reversed. Inflow conduit 172 has a smaller diameter than lumen 166 leaving an annular gap 169 therebetween to permit the return of fluid to return conduit 174. As such, during cooling, fluid, e.g., water, saline, etc., is pumped through inflow conduit 172, exits a distal end of inflow conduit 172 at the distal end of lumen 166, and travels proximally back through lumen 166 within annular gap 169, ultimately being received by return conduit 174 for return to cooling module 500 (FIG. 1). Inflow and return conduits 172, 174 are at least partially formed from polyimide tubing. However, as it has been found that the portion of inflow conduit 172 that extends distally through lumen 166 may be subject to delamination and, as a flow, may block the flow of fluid during use. As such, in embodiments, the portion of inflow conduit 172 that extends distally through lumen 166 is formed from stainless steel or other material suitable to withstand high temperatures. Further, in embodiments where blade 162 is curved, the portion of inflow conduit 172 that extends distally through lumen 166 is likewise curved so as not to rub on the interior surface of blade 162.

Figure 4:
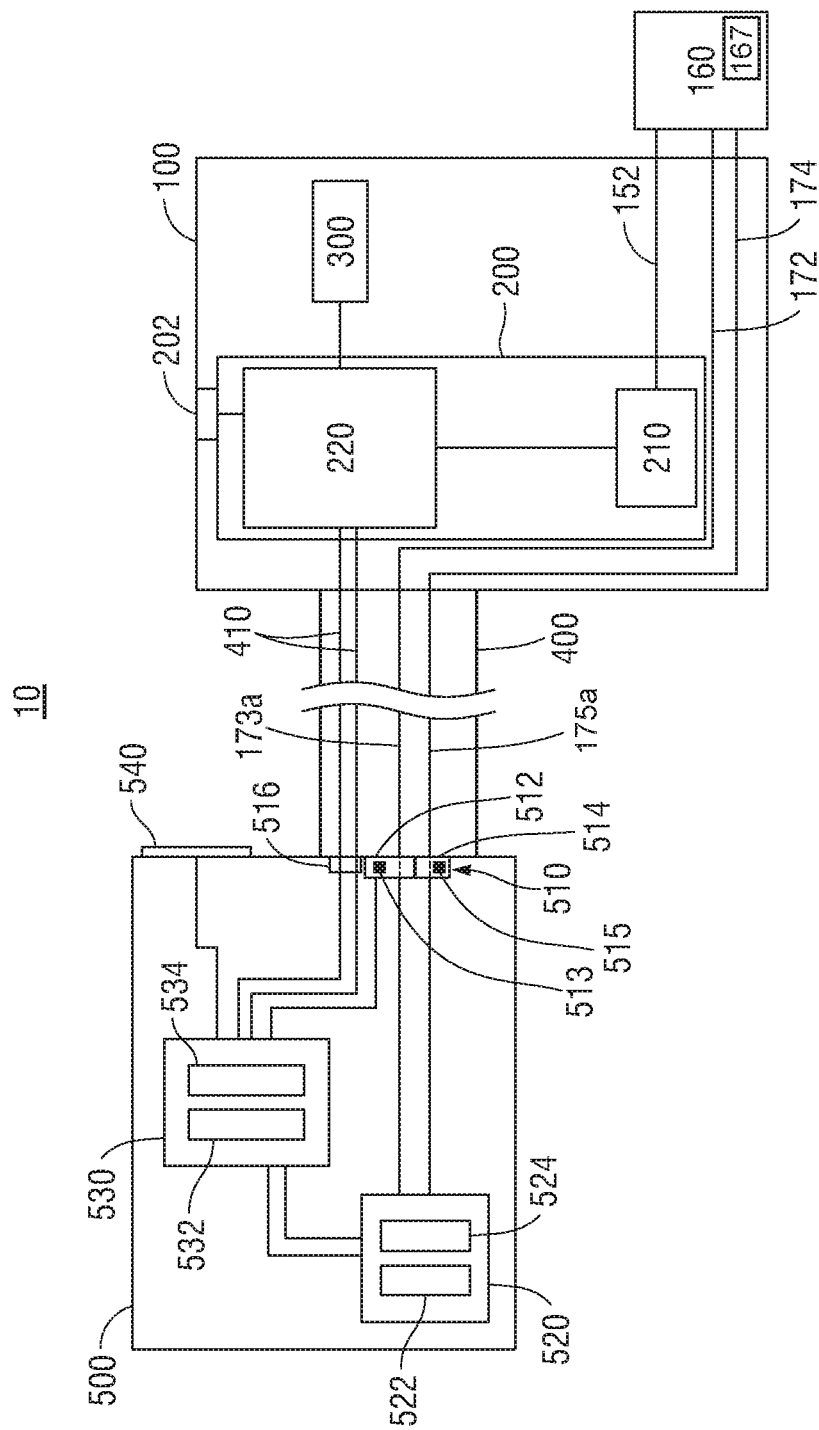
FIG. 4 is a schematic illustration of the surgical system of FIG. 1 depicting the internal operating components of the cooling system thereof.

Referring to FIG. 4, cooling module 500 includes an input port 510, a pump assembly 520, a controller 530, and a user interface 540. Input port 510 enables operable coupling of cable 400 with cooling module 500. More specifically, input port 510 includes an inflow conduit receptacle 512, a return conduit receptacle 514, and one or more electrical receptacles 516. Inflow conduit receptacle 512 operably couples inflow conduit 172 with pump assembly 520 upon engagement of cable 400 with cooling module 500, return conduit receptacle 514 operably couples return conduit 174 with pump assembly 520 upon engagement of cable 400 with cooling module 500, and the electrical receptacles 516 operably couple TAG 200 with controller 530, via wires 410, upon engagement of cable 400 with cooling module 500.

Inflow and return conduit receptacles 512, 514 each include one or more sensors 513, 515, respectively, associated therewith for sensing the temperature of fluid flowing therethrough, the flow rate of fluid therethrough, and/or the presence of gas bubbles flowing therethrough, as detailed below.

Pump assembly 520 includes a fluid reservoir 522 and a pump 524 and is coupled between inflow conduit 172 and return conduit 174. Fluid reservoir 522 stores fluid to be circulated through conduits 172, 174 and lumen 166 to cool blade 162 of end effector assembly 160 (see FIG. 3) after use. In some embodiments, fluid reservoir 522 may be configured to regulate the temperature of the fluid retained therein. Further, instead of a closed system utilizing fluid reservoir 522, an open system may be provided wherein fluid to be circulated is received from an external fluid source (not shown), and fluid returning is output to a drain or return reservoir (not shown).

Pump 524 is configured as a pull-pump, wherein pump 524 operates to pull fluid through conduits 172, 174 and lumen 166. A pull-pump configuration is advantageous in that pressure build-up in push-pump configurations, e.g., due to an obstruction along the fluid flow path, is avoided. However, in some embodiments, pump 524 may be configured as a push-pump. Pump 524 may be a peristaltic pump, or any other suitable pump.

Continuing with reference to FIG. 4, controller 530 of cooling module 500 includes a processor 532 and a memory 534 storing instructions for execution by processor 532. Controller 530 is coupled to pump assembly 520, sensors 513, 515, TAG 200 (via wires 410 extending through cable 400), and user interface 540. Controller 530 may be configured to implement the method of FIG. 10A or 10B so as to instruct pump assembly 520 to turn pump 524 ON or OFF, to thereby initiate or stop blade cooling, based at least upon feedback received from sensors 513, 515, TAG 200, or other received feedback. As detailed below, controller 532 may be configured so as to instruct pump assembly 520 to turn OFF pump 524 where sensor 515 indicates a sufficiently low temperature of fluid returning from return conduit 174. The temperature of blade 162 (FIG. 3) of end effector assembly 160 may be extrapolated from the temperature of fluid returning from fluid conduit 174, or the temperature difference between the fluid entering inflow conduit 172 and that returning from return conduit 174, and, accordingly, pump 524 may be turned OFF upon blade 162 reaching a sufficiently cool temperature, e.g., below about 60° C. (or other suitable temperature threshold), as indicated by a sufficiently low return fluid temperature or sufficiently small temperature differential. As an alternative to sensors 513, 515 sensing temperature at input port 510, temperature sensors may be incorporated into pump assembly 520 for similar purposes as noted above. Further, in embodiments, a thermocouple 167 (FIG. 4) or other suitable temperature sensor may additionally or alternatively be incorporated into blade 162 (see, for example, thermocouple 2173 (FIG. 7)) to enable the sensing of temperature at blade 162.

Controller 530, as also detailed below with respect to FIGS. 10A and 10B, may additionally or alternatively instruct pump assembly 520 to turn OFF pump 524 or disable the entire system where sensor 513 and/or sensor 515 indicates an error. Such errors may include, for example, where sensor 513 and/or sensor 515 detects a flow rate through inflow conduit 172 and/or return conduit 174 below a threshold flow rate, and/or where sensor 515 detects gas bubbles, or a gas bubble volume greater than a threshold volume, returning from return conduit 174. Reduced flow rate and/or the presence of gas bubbles (or a greater volume of gas bubbles) may be an indication of a blockage or leak within the fluid flow path or damage to one of the conduits 172, 174 and, thus, the circulation of fluid is stopped by turning OFF pump 524 when such is detected. As noted above, in embodiments, rather than just turning OFF pump 524, the entire system is disabled, thereby inhibiting further use permanently or until the error or problem is remedied.

Controller 530 may further be configured, as also detailed below with respect to FIGS. 10A and 10B, to output an appropriate signal to user interface 540 and/or indicator 202 of TAG 200 to alert the user that blade cooling is in effect, e.g., that pump 524 is ON, that an error, e.g., a blockage or leakage, has occurred, and/or that blade 162 (FIG. 3) has been sufficiently cooled and is ready for further use. User interface 540 and/or indicator 202 may provide such an alert in the form of audible, visual, and/or tactile output.

Controller 530 may, additionally or alternatively, as also detailed below with respect to FIGS. 10A and 10B, be configured to communicate with TAG 200 to determine whether endoscopic ultrasonic surgical instrument 100 is in use, e.g., whether activation button 140 is actuated such that ultrasonic energy is being supplied to blade 162 (see FIG. 1), and to control pump assembly 520 in accordance therewith. More specifically, controller 530 may instruct pump assembly 520 to turn OFF pump 524 when endoscopic ultrasonic surgical instrument 100 is in use. Once use is complete, pump 524 may be turned ON for a pre-determined time, until blade 162 has been sufficiently cooled, until an error is detected, or until endoscopic ultrasonic surgical instrument 100 is once again put into use.

Controller 530 may further communicate with TAG 200 to control the cooling system and/or determine whether the cooling system is operating normally based on the frequency of the transducer 210 and/or waveguide 152 (FIG. 3). Thus, TAG 200 provides, e.g., via wires 410, the frequency of the transducer 210 and/or waveguide 152 (FIG. 3) to the controller 530. This frequency information is useful in that it is indicative of the state of the system. More specifically, it has been found that during use, e.g., during tissue treatment, the frequency decreases, while, upon deactivation and release of tissue, the frequency increases. It has further been found that, if waveguide 152 is cooled shortly after deactivation and release of tissue, the frequency increases at a significantly greater rate as compared to an un-cooled waveguide 152. Thus by monitoring the rate of change in frequency, e.g., by monitoring deviation of the rate of change relative to a threshold value or threshold range, controller 530 can determine whether the cooling system is working to effectively cool waveguide 152, or whether cooling is ineffective or inoperable. Such may be used in addition to or in place of temperature sensors. For example, the frequency information may be used, in conjunction with the flow rate information from sensors 513, 515, to determine whether cooling is working properly, based upon the flow rates and frequency rate of change, without the need to directly monitor temperature.

Figure 5:
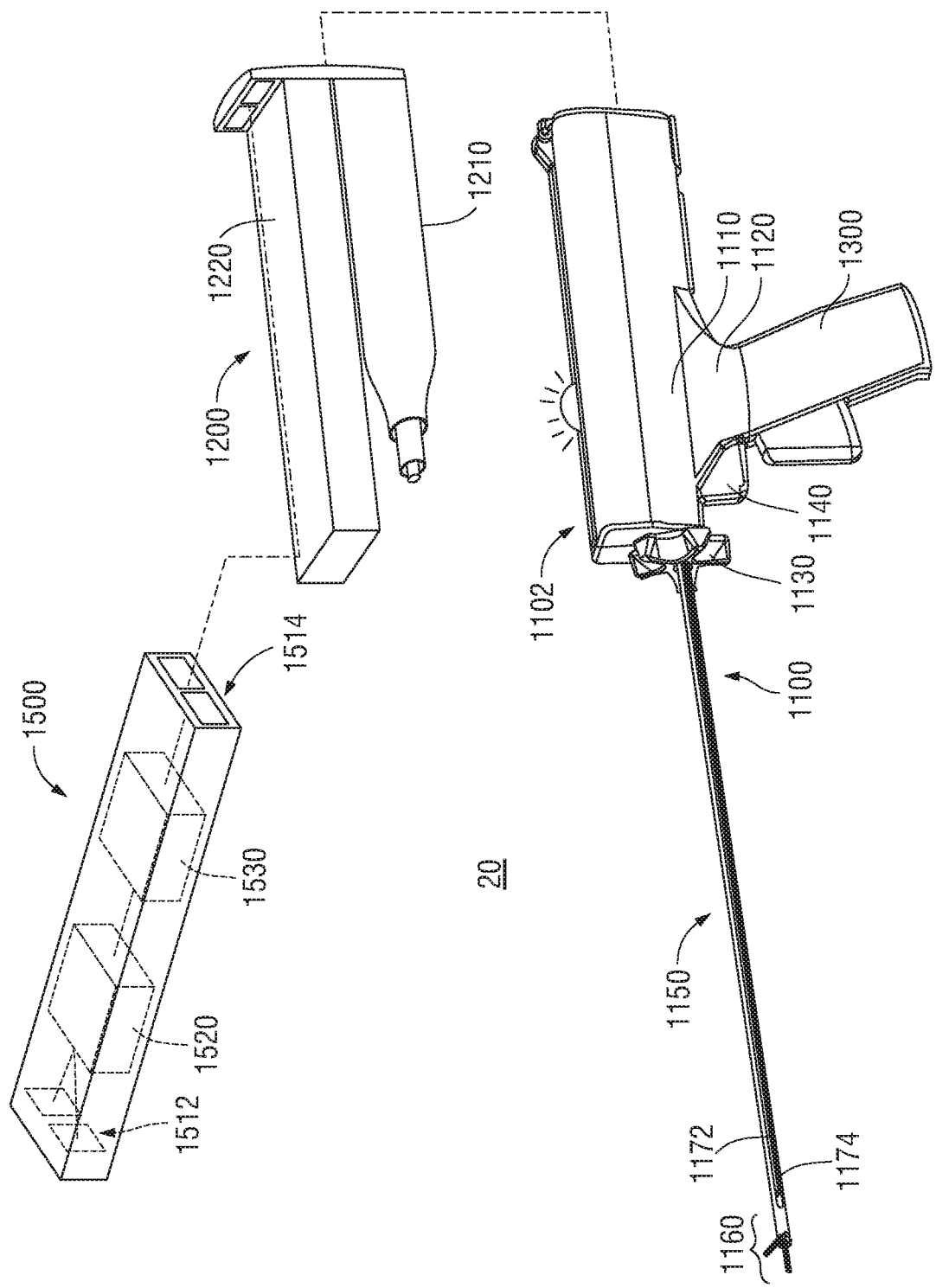
FIG. 5 is an exploded, perspective view of another surgical system provided in accordance with the present disclosure including a handheld endoscopic ultrasonic surgical instrument ultrasonic surgical instrument including an on-board cooling module and having a cooling system incorporated therein.

Turning now to FIG. 5, surgical system 20 is similar to surgical system 10 (FIG. 1) and generally includes an endoscopic ultrasonic surgical instrument 1100 and a cooling module 1500. However, rather than being coupled via a cable 400 as with endoscopic ultrasonic surgical instrument 100 and cooling module 500 (FIG. 1), instrument 1100 includes cooling module 1500 disposed thereon, e.g., formed as part of disposable 1102 or releasably mounted thereon.

Instrument 1100 generally includes a disposable 1102, a transducer and generator assembly ("TAG") 1200 including a transducer 1210 and a generator 1220, and a battery 1300. Disposable 1102 includes a housing 1110, a handle assembly 1120, a rotating assembly 1130, an activation button 1140, an elongated body portion 1150, and an end effector assembly 1160, each of which are similar to the corresponding components of instrument 100 (FIG. 1), detailed above. TAG 1200 and battery 1300 are releasably engagable with housing 1110 of disposable 1102 and, when engaged therewith, are disposed in electrical communication with one another such that power and/or control signals can be relayed between TAG 1200 and battery 1300 for operating instrument 1100. TAG 1200 and battery 1300 are similar to those detailed above with respect to instrument 100 (FIG. 1), except as otherwise noted below.

Cooling module 1500, similar as with cooling module 500 (FIG. 4), includes input ports 1512, 1514, a pump assembly 1520, and a controller 1530. Cooling module 1500 may be permanently mounted on TAG 1200, may be releasably engagable with both TAG 1200 and disposable 1102, or may be permanently mounted on or within disposable 1102. Input port 1512 enables operable coupling of pump assembly 1520 with the conduits 1172, 1174 of instrument 1100, while input port 1514 enables communication between controller 1530 and generator 1220, both of which are similar as detailed above with respect to input port 510 (FIG. 4). Pump assembly 1520 and controller 1530 are also similar as detailed above, and may be configured to operate in a similar manner as mentioned above and as described in greater detail below.

Turning now to FIGS. 6-9, another instrument provided in accordance with the present disclosure, an open ultrasonic surgical instrument 2100, is detailed. Open ultrasonic surgical instrument 2100 is configured to operably coupled to a table-top generator (or other remote generator) (not shown) and a cooling module (similar to cooling module 500). In some embodiments, the generator and cooling module are integrated into a single housing (not shown). Open ultrasonic surgical instrument 2100 generally includes two elongated shaft members 2110a, 2110b, an activation button 2140, an elongated body portion 2150, an end effector assembly 2160, a tube assembly 2170, and a transducer assembly 2200.

Figure 6:
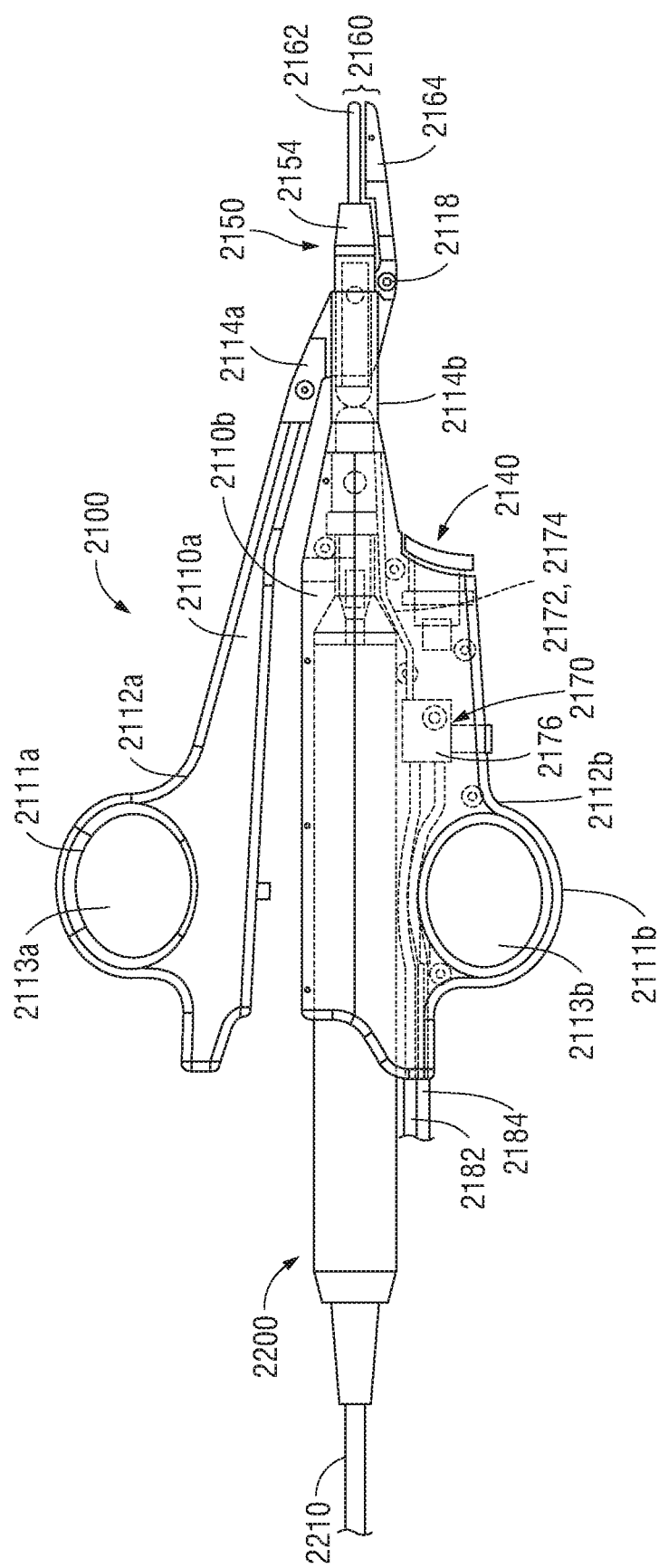
FIG. 6 is a side, cross-sectional view of an open ultrasonic surgical instrument provided in accordance with the present disclosure and including a cooling system configured for use therewith.

Referring to FIG. 6, each shaft member 2110a, 2110b includes a handle 2111a, 2111b disposed at the proximal end 2112a, 2112b thereof. Each handle 2111a, 2111b defines a finger hole 2113a, 2113b therethrough for receiving a finger of the user. One of the shaft members, e.g., shaft member 2110a, includes a jaw member 2164 of end effector assembly 2160 extending from the distal end 2114a thereof. The other shaft member, e.g., shaft member 2110b, supports elongated body portion 2150 and transducer assembly 2200 thereon. Shaft members 2110a, 2110b are pivotably coupled to one another towards the distal ends 2114a, 2114b, respectively, thereof via a pivot pin 2118.

Elongated body portion 2150 of shaft member 2110b includes a waveguide 2152 (FIGS. 8A and 8B) which extends from transducer assembly 2200 to end effector assembly 2160, and an outer sleeve 2154 surrounding waveguide 2152. The distal end of waveguide 2152 extends distally from outer sleeve 2154 and defines a blade 2162 of end effector assembly 2160, while the proximal end of waveguide 2152 is operably coupled to transducer assembly 2200. Due to the pivotable coupling of shaft members 2110a, 2110b towards the distal ends 2114a, 2114b, respectively, thereof, handles 2111a, 2111b may be pivoted relative to one another to thereby pivot jaw member 2164 relative to blade 2162 between an open position, wherein jaw member 2164 is spaced-apart from blade 2162, and a closed position, wherein jaw member 2164 is approximated relative to blade 2162 in juxtaposed alignment therewith for clamping tissue therebetween.

Transducer assembly 2200 is configured to convert electrical energy provided by the generator (not shown) and supplied via cable 2210, into mechanical energy that is transmitted along waveguide 2152 to blade 2162. Transducer assembly 2200 may be permanently affixed to elongated body portion 2150 or may be removable therefrom. Activation button 2140 is disposed on one of the shaft members, e.g., shaft member 2110b, and, similarly as detailed above with respect to instrument 100 (FIG. 1), is selectively activatable in a first position and a second position to supply electrical energy to transducer assembly 2200 for operating instrument 2100 in a low-power mode of operation and a high-power mode of operation, respectively.

Figure 7:
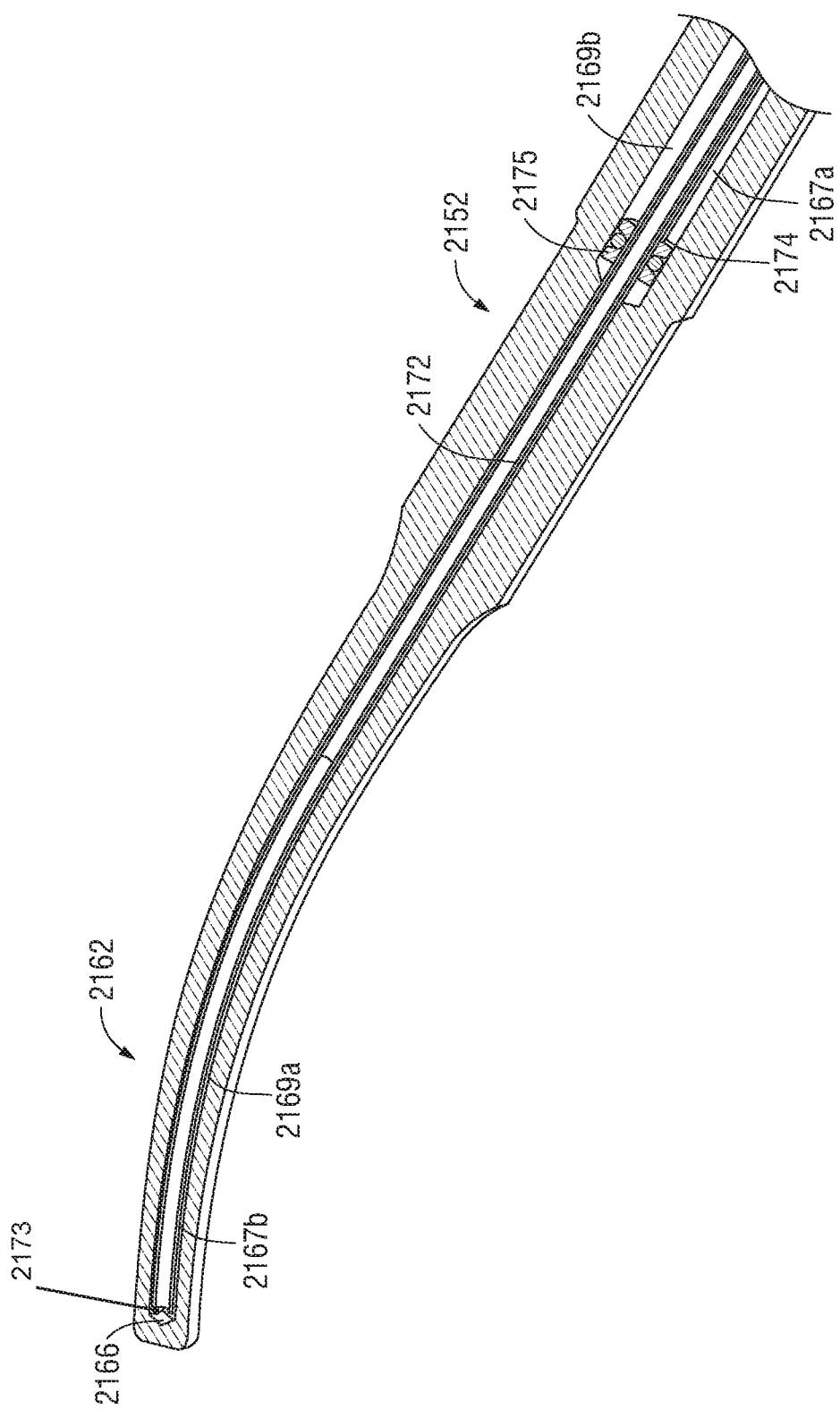
FIG. 7 is an enlarged, top, cross-sectional view of the blade of the surgical instrument of FIG. 6.
Figure 8A:
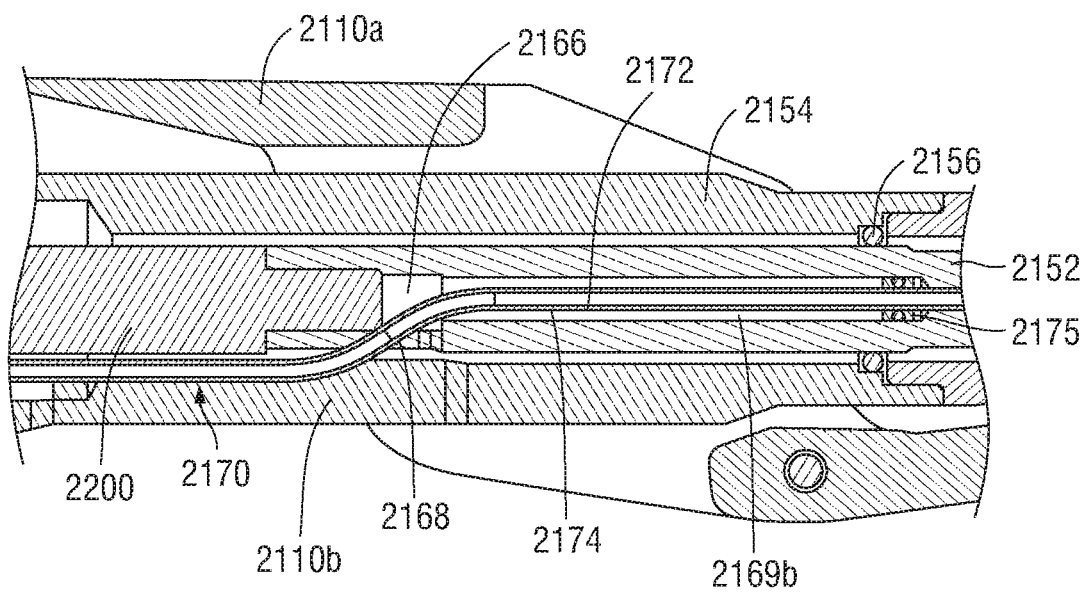
FIG. 8A is an enlarged, side, cross-sectional view of a portion of the surgical instrument of FIG. 6, illustrating routing of the cooling conduits into and through the waveguide of the surgical instrument.
Figure 8B:
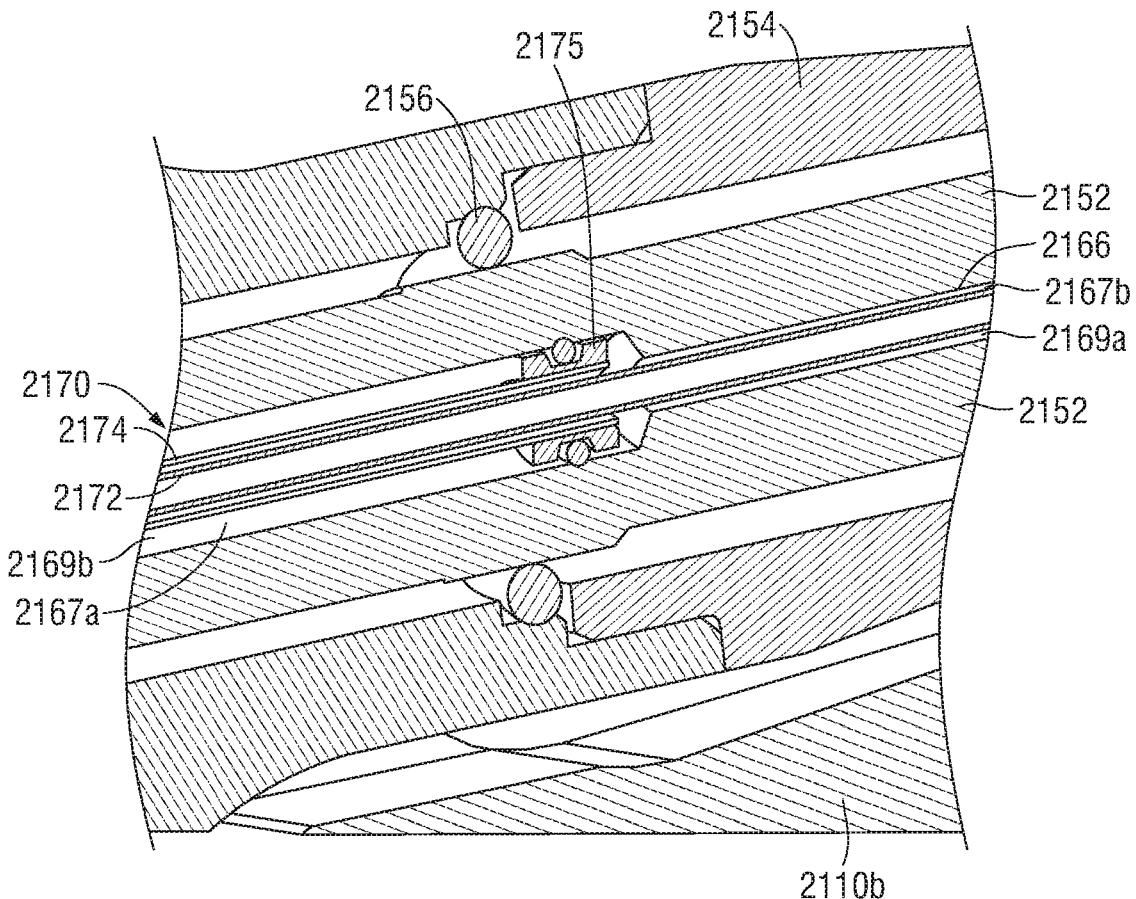
FIG. 8B is a greatly enlarged, side, cross-sectional view of a portion of the surgical instrument of FIG. 6, illustrating the routing of the cooling conduits through the waveguide of the surgical instrument.

With reference to FIGS. 7 and 8A-8B, elongated body portion 2150 is described in greater detail. As noted above, elongated body portion 2150 includes waveguide 2152 and outer sleeve 2154. The distal end of waveguide 2152 extends distally from outer sleeve 2154 and defines blade 2162. Waveguide is secured within outer sleeve 2154 via an O-ring 2156 (FIGS. 8A and 8B). As shown in FIG. 7, blade 2162 defines a curved configuration. Blade 2162 may be curved in any direction relative to jaw member 2164, for example, such that the distal tip of blade 2162 is curved towards jaw member 2164, away from jaw member 2164, or laterally (in either direction) relative to jaw member 2164. Waveguide 2152 and blade 2162 may include any of the features of waveguide 152 and blade 162 (see FIG. 3), and vice versa. Further, waveguide 2152 and blade 2162 may be used with instrument 100 (FIG. 1), or any other suitable instrument, and, likewise, waveguide 152 and blade 162 (see FIG. 3) may be used with instrument 2100 (FIG. 6), or any other suitable instrument.

Referring again to FIGS. 7 and 8A-8B, waveguide 2152 defines a lumen 2166 therethrough that extends into blade 2162. Lumen 2166 is open at its proximal end, the proximal end of waveguide 2152, and closed at its distal end, the closed distal end of blade 2162. Connection between waveguide 2152 and transducer assembly 2200 at the proximal end of waveguide 2152 serves to close off the proximal end of lumen 2166 (see FIG. 8A). Lumen 2166 defines a proximal segment 2167a having the open proximal end and defining a first diameter, and a distal segment 2167b having the closed distal end and defining a second diameter smaller than the first diameter.

Figure 9:
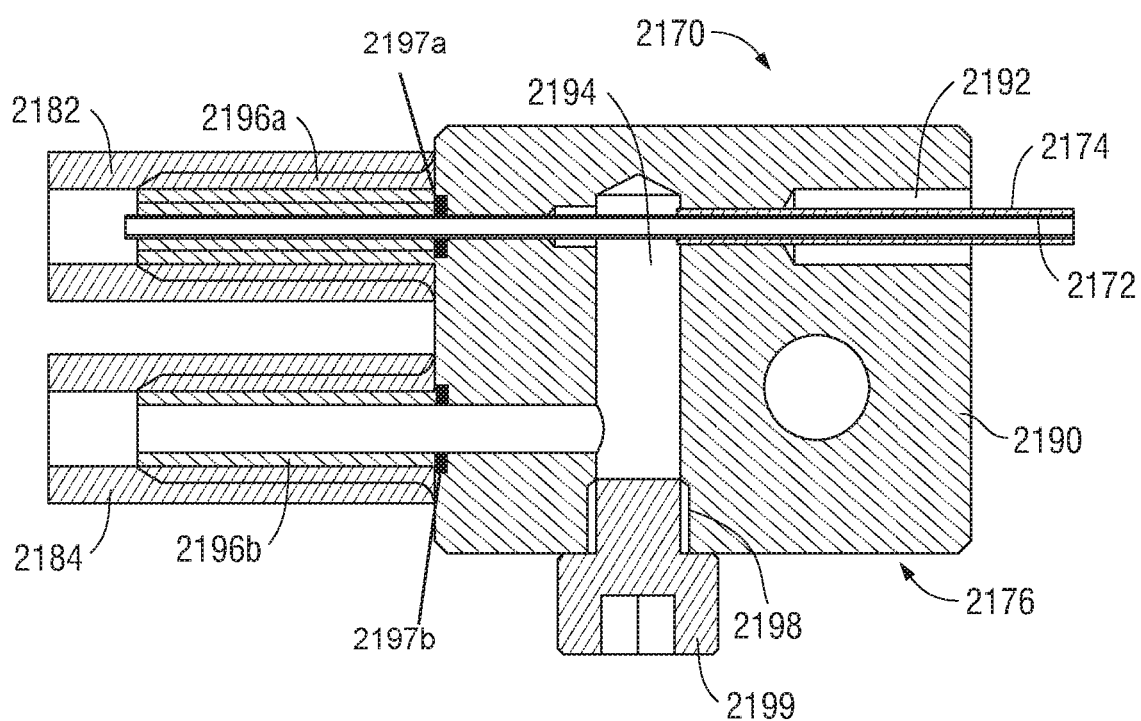
FIG. 9 is an enlarged, side view illustrating coupling of the cooling conduits of the surgical instrument of FIG. 6 with a tube splitter of the surgical instrument to enable the supply and return of cooling fluid from the surgical instrument.

Tube assembly 2170 (FIG. 6) includes inflow and return conduits 2172, 2174, respectively, and a tube splitter 2176 (FIG. 9). Conduits 2172, 2174 are arranged such that conduit 2174 is coaxially disposed about conduit 2172. Conduits 2172, 2174 enter proximal segment 2167a of lumen 2166, in the above-noted coaxial arrangement, through an opening 2168 disposed in communication with lumen 2166. Inflow conduit 2172 extends distally from return conduit 2174 through proximal segment 2167a of lumen 2166 into distal segment 2167b of lumen 2166 to the distal end of blade 2162. Inflow conduit 2172 has a smaller diameter than distal segment 2167b of lumen 2166 leaving an annular gap 2169a therebetween to permit the return of fluid to return conduit 2174. Return conduit 2174 does not extend into distal segment 2167b of lumen 2166. Rather, a ferrule 2175 is disposed about return conduit 2174 at the distal end of proximal segment 2167b of lumen 2166 so as to seal an annular gap 2169b of lumen 2166 surrounding return conduit 2174. As such, during cooling, fluid is pumped through inflow conduit 2172, exits a distal end of inflow conduit 2172 at the distal end of lumen 2166, and travels proximally back through lumen 2166 within annular gap 2169a, ultimately being received by return conduit 2174. Ferrule 2175 inhibits further proximal flow of cooling fluid, e.g., into annular gap 2169b, thus ensuring that the returning fluid enters return conduit 2174.

Referring to FIG. 9, tube splitter 2176 of tube assembly 2170 is disposed within one of the shaft members, e.g., shaft member 2110b, of instrument 2100 (see FIG. 6). Tube splitter 2176 receives the proximal ends of conduits 2172, 2174 which, as noted above, are coaxially disposed relative to one another, and routes the flow of fluid to/from conduits 2172, 2174 and respective connector tubes 2182, 2184. Connector tubes 2182, 2184, in turn, are coupled with a cooling module (not shown, similar to cooling module 500 (FIG. 1)) to enable the inflow and outflow of cooling fluid to/from conduits 2172, 2174, similarly as detailed above with respect to instrument 100 (FIG. 1).

Tube splitter 2176 generally includes a housing 2190 defining a conduit port 2192, an interior chamber 2194, input and output ports 2196a, 2196b, respectively, and an auxiliary port 2198. Conduit port 2192 receives the proximal ends of conduits 2172, 2174 which, as noted above, are disposed in coaxial relation relative to one another. Return conduit 2174 is sealingly engaged within conduit port 2192 so as to inhibit the escape of fluid therebetween. Return conduit 2174 terminates at interior chamber 2194 and is disposed in fluid communication with interior chamber 2194. Inflow conduit 2172 extends through interior chamber 2194 and into input port 2196a, wherein inflow conduit 2172 is sealingly engaged. Connector tube 2182 is sealingly engaged about input port 2196a. Thus, fluid flowing through connector tube 2182 is routed into inflow conduit 2172 and, ultimately, through lumen 2166 (FIG. 7) of waveguide 2152 and blade 2162 (FIG. 7). Connector tube 2184 is sealingly engaged about output port 2196b, which communicates with chamber 2194. As such, fluid flowing through return conduit 2174 ultimately flows into chamber 2194 and, thereafter, out through output port 2196b to connector tube 2184. However, it is also contemplated that inflow and return conduits 2172, 2174, respectively, be reversed, and, thus, that fluid flows in the opposite direction. Auxiliary port 2198 communicates with chamber 2194 and includes a stopper 2199 sealingly engaged therein.

Tube splitter 2176 further includes sensors 2197a, 2197b disposed adjacent input and output portion 2196a, 2196b, respectively, although sensors 2197a 2197b may be positioned at any suitable position on or along instrument 2100 or the components thereof, e.g., the waveguide 2152, blade 2162, inflow and return conduits 2172, 2174, transducer assembly 2200, etc. (see FIGS. 6-8B). Sensors 2197a, 2197b may be configured as thermocouples for sensing temperature and/or may otherwise be configured similar to sensors 513, 515 (FIG. 4), respectively, to, as noted above, sense the temperature of fluid flowing therethrough, the flow rate of fluid therethrough, and/or the presence of gas bubbles flowing therethrough.

Referring to FIGS. 1 and 9, although detailed above with respect to instrument 2100 (FIG. 6), tube splitter 2176 and connector tubes 2182, 2184 may similarly be used in connection with instrument 100, serving to couple cooling module 500 and conduits 172, 174. In such a configuration, tube splitter 2176 is mounted within housing 110 of disposable 102 so as to receive the proximal ends of conduits 172, 174. Connector tubes 2182, 2184, in such a configuration, would extend through cable 400 for coupling with cooling module 500. Instrument 100 would otherwise be configured similarly as detailed above and would function in a similar manner as detailed above and described in further detail below.

Figure 10A:
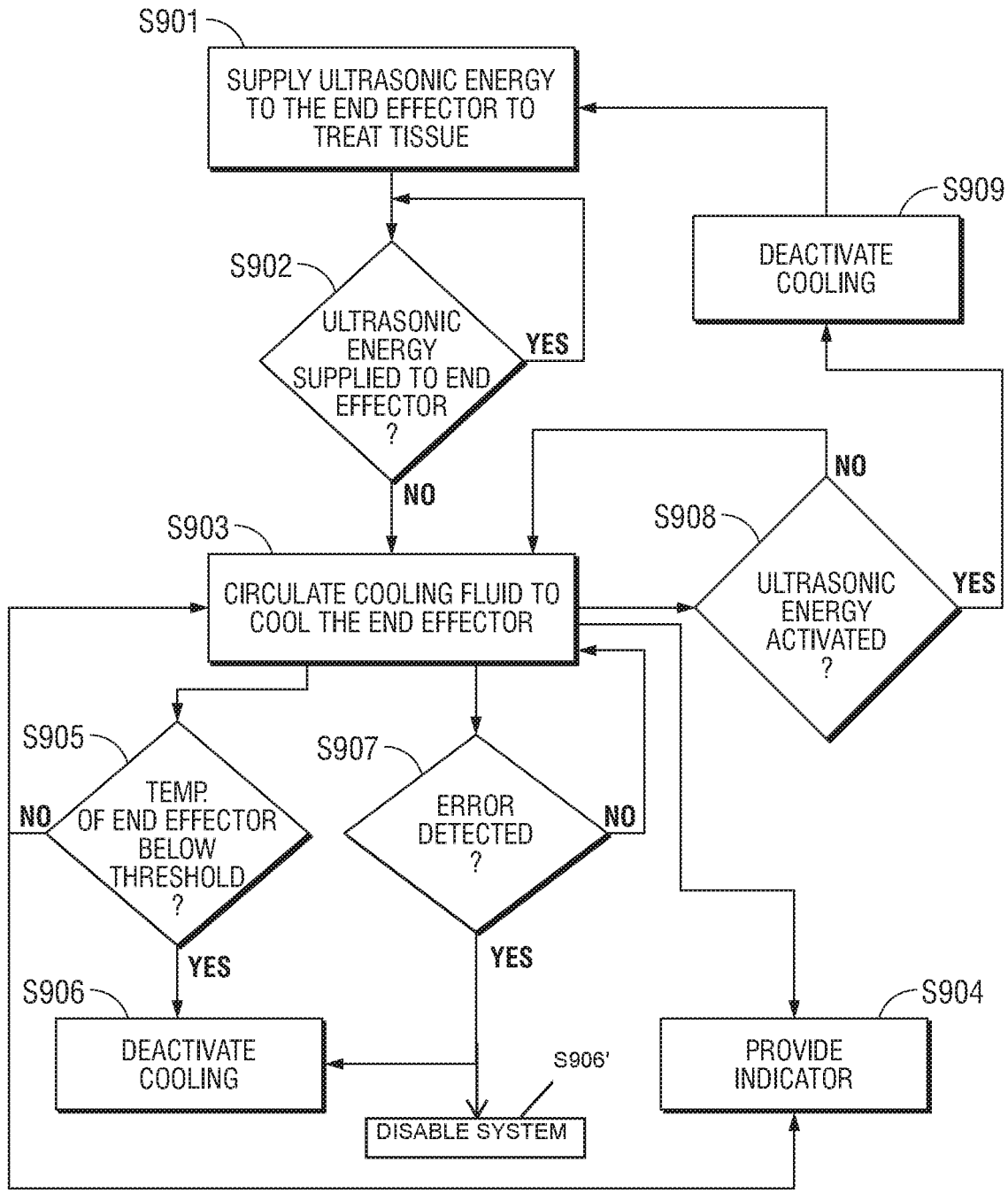
FIG. 10A is a flow diagram depicting a method of cooling a surgical instrument provided in accordance with the present disclosure.

Turning now to FIG. 10A, a method provided in accordance with the present disclosure, and applicable for use with instrument 100 (FIG. 1), instrument 1100 (FIG. 5), instrument 2100 (FIG. 6), or any other suitable ultrasonic surgical instrument incorporating or configured for use with a cooling system is described.

Initially, at S901, the end effector of the instrument is activated so as to supply ultrasonic energy to the end effector thereof to treat, for example, coagulate and/or cut, tissue. At S902 it is determined whether ultrasonic energy is still being supplied to the end effector. Such a determination may be performed, as noted above, by determining whether an activation button is activated. However, other suitable ways of determining whether ultrasonic energy is being supplied to the end effector are also contemplated, e.g., monitoring the output of the battery or the input to or output from the transducer. If it is determined that ultrasonic energy is being supplied, the determination at S902 is repeatedly made, periodically or continuously, until it is determined that ultrasonic energy is no longer being supplied to the end effector.

Once it is determined that ultrasonic energy is no longer being supplied to the end effector, the cooling system is activated as indicated in S903, to circulate cooling fluid through the end effector to cool the end effector. Likewise, an indicator S904 is provided to indicate that cooling is ongoing. During cooling, it is determined, at S905, whether the temperature of the end effector is below a threshold temperature. As noted above with respect to instrument 100 (FIG. 1), the temperature of the end effector may be determined indirectly by sensing the temperature of the fluid output to the end effector and returning therefrom. Such a configuration enables the use of temperature sensors remote from the end effector.

If the temperature of the end effector is determined to be above the threshold temperature, cooling continues at S903 and the temperature is continuously or periodically determined at S905. At the same time, an indicator, as indicated in S904, is provided to alert the user that cooling is still ongoing. Once the temperature of the end effector assembly is below the threshold temperature, as indicated in S906, cooling is deactivated and the indicator is removed. The threshold temperature, in some embodiments, may be about 60° C.

Referring to S907, during cooling, if an error is detected, cooling is deactivated at S906 and an indicator is provided at S904. Alternatively, the entire system may be shut down, inhibiting further activation or use, as indicated at S906'. An error may include, as noted above, a condition where the flow rate of fluid is below a flow rate threshold, a condition where the fluid includes gas bubbles or a sufficiently high volume of gas bubble, or other suitable error condition. The indicator provided in response to an error may be different from the indicator provided during cooling. If no error is detected, cooling continues at S903.

Turning to S908, during cooling, it is determined whether the supply of ultrasonic energy to the end effector has been activated. If so, cooling is deactivated at S909 and the method returns to S901. If the supplying of ultrasonic energy to the end effector has not been activated, the method returns to S903 and cooling is continued until the temperature of the end effector is below the threshold temperature, an error is detected, or the supply of ultrasonic energy to the end effector is activated.

Figure 10B:
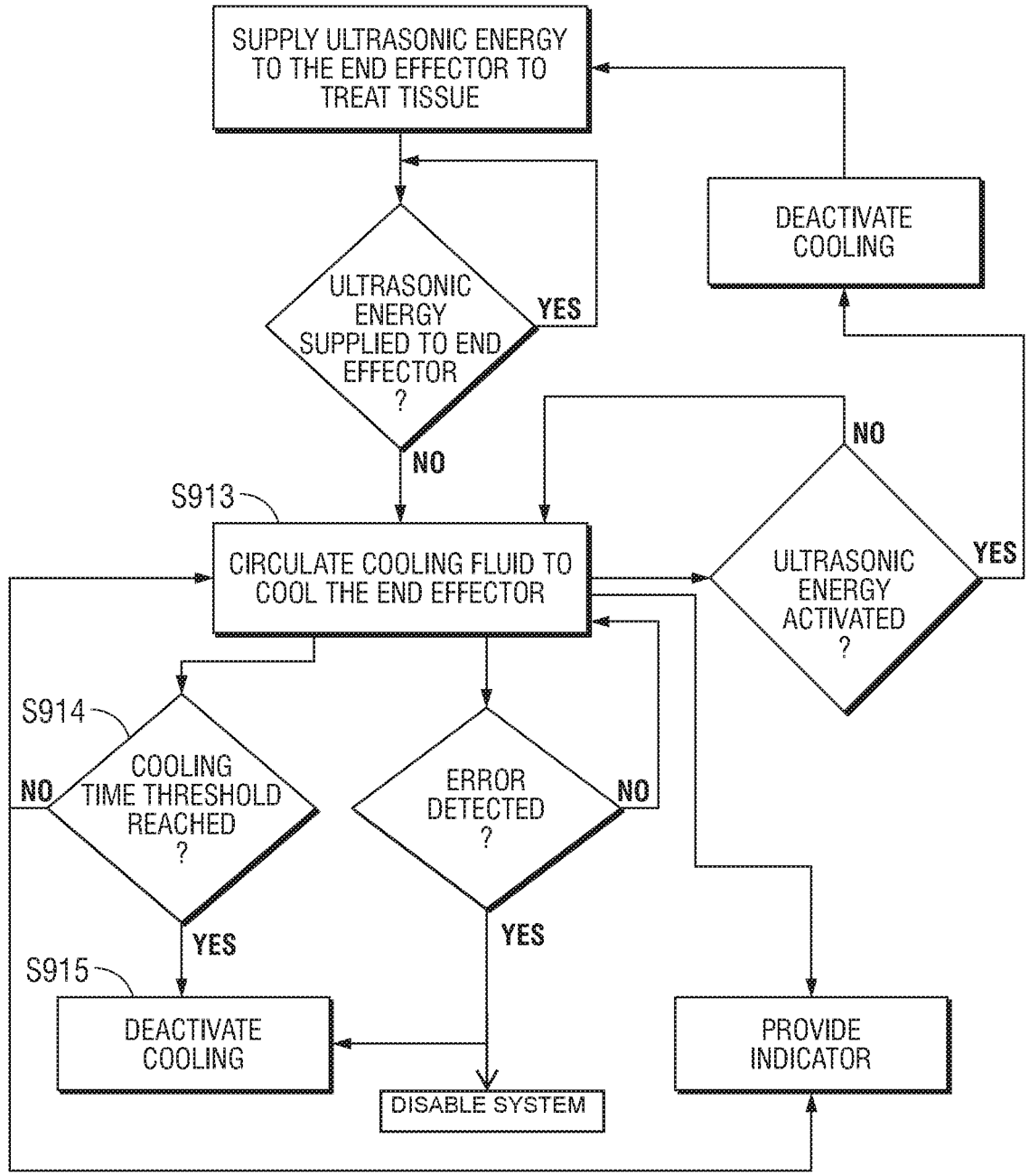
FIG. 10B is a flow diagram depicting another method of cooling a surgical instrument provided in accordance with the present disclosure.

Referring to FIG. 10B, another method provided in accordance with the present disclosure, and applicable for use with instrument 100 (FIG. 1), instrument 1100 (FIG. 5), instrument 2100 (FIG. 6), or any other suitable ultrasonic surgical instrument incorporating or configured for use with a cooling system is described.

The method of FIG. 10B is similar to that of FIG. 10A except that, during cooling, S913, it is determined at S914 whether the time cooling has been activated has reached a threshold time. If the cooling time has reached the threshold time, cooling is deactivated at S915. If the cooling time has not reached the threshold time, cooling continues at S913. Determination of the cooling time may be based upon an uninterrupted duration of cooling, a cumulative amount of cooling since the last energization of the end effector, or in any other suitable manner.

Figure 11:
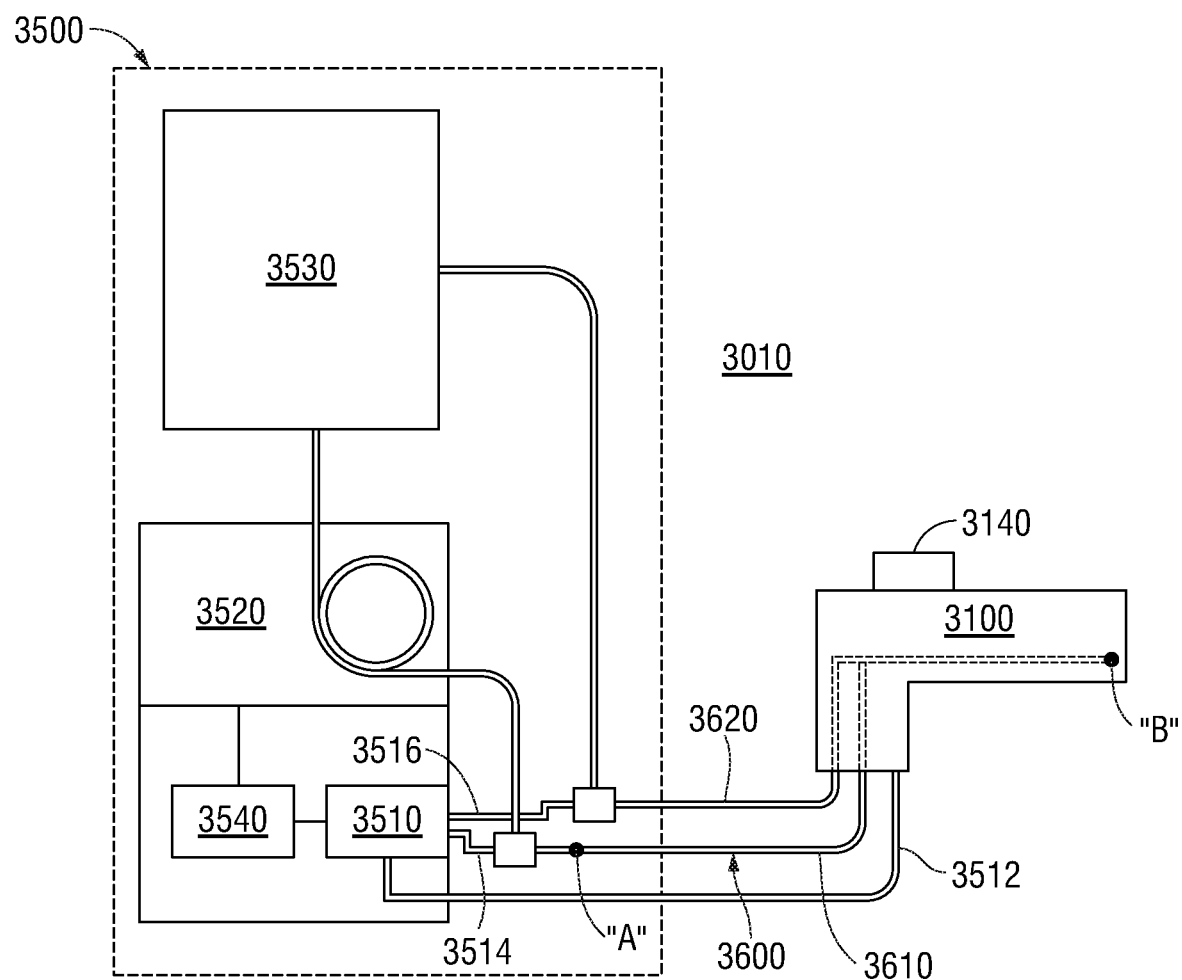
FIG. 11 is a schematic illustrating of another cooling system provided in accordance with the present disclosure, depicting the internal operating components of the cooling system.

Turning to FIG. 11, another surgical system for cooling a surgical instrument provided in accordance with the aspects and features of the present disclosure is shown generally identified by reference numeral 3010. Surgical system 3010, as detailed below, is configured for use with a conductive cooling fluid circulating through the instrument so as to enable measurement of the electrical impedance thereof to provide an indication of events that may occur during use, for example, determination of the whether the system is properly primed, detection of mechanical failure, detection of obstruction(s) in the flowpath, detection of gas bubbles in the flowpath, determining whether cooling is operating normally, etc. Surgical system 3010 may include any of the features of the surgical systems detailed above, and vice-versa. Accordingly, only those distinguishing features and those necessary to facilitate the understand of surgical system 3010 are described in detailed below.

Surgical system 3010 generally includes a surgical instrument 3100, a cooling module 3500, and a cooling fluid flowpath 3600 defined therebetween, e.g., via tubing, conduits, etc., that, together, incorporate a cooling system for cooling surgical instrument 3100. Surgical instrument 3100 may be configured similar to surgical instrument 100 (FIG. 1), surgical instrument 1100 (FIG. 5), surgical instrument 2100 (FIG. 6), or any other suitable surgical instrument. Inflow line 3610 of flowpath 3600 is configured to deliver conductive cooling fluid from cooling module 3500 to surgical instrument 3100, while outflow line 3620 of flowpath 3600 is configured to return conductive cooling fluid from surgical instrument 3100 to cooling module 3500.

Cooling module 3500 may be separate from surgical instrument 3100 (as with cooling module 500 (FIG. 1)) or may be integrated into surgical instrument 3100 (as with cooling module 1500 (FIG. 5)). Cooling module 3500 includes a generator 3510, a pump assembly 3520, a fluid reservoir 3530 retaining a conductive cooling fluid therein, and a controller 3540. Generator 3510 is electrically coupled to instrument 3100, e.g., via one or more wires 3512, for supplying energy thereto. Where instrument 3100 is an ultrasonic instrument, for example, generator 3510 supplies suitable energy to the transducer (not shown) of instrument 3100 to drive the transducer. Generator 3510 further includes electrodes 3514, 3516 that are disposed in communication with the conductive cooling fluid adjacent the output from cooling module 3500 to instrument 3100 (location "A") and towards the distal tip of instrument 3100 (location "B"), respectively. Electrodes 3514, 3516 may extend through inflow line 3610 and/or outflow line 3620 to respective locations "A" and "B," as shown, may extend exteriorly of inflow line 3610 and/or outflow line 3620 and electrically couple to the conductive cooling fluid by way of one or more conductive couplings (not shown) at respective locations "A" and "B," and/or may extend through a side wall of inflow line 3610 and/or outflow line 3620 into communication with the conductive cooling fluid at respective locations "A" and "B" with a seal disposed thereabout for sealing the opening in the side wall of inflow line 3610 and/or outflow line 3620. Based upon electrical properties of the conductive cooling fluid detected by electrodes 3514, 3516, generator 3510 is capable of determining the impedance of the conductive cooling fluid between locations "A" and "B." The determined impedance can then be relayed to controller 3540 for outputting an indication of various events and/or controlling system 3010 accordingly, as detailed below. Additional or alternative locations for determining impedance therebetween are also contemplated, for example, the electrodes may be positioned as detailed in any or all of the above systems with respect to the sensors thereof.

Pump assembly 3520 may include any suitable pump, such as those detailed above, suitable for pumping conductive cooling fluid to circulate from cooling module 3500, through instrument 3100, and back to cooling module 3500. Controller 3540 may control pump assembly 3520 to turn the pump "ON" and "OFF," to pump the conductive cooling fluid at a particular flow rate and/or to achieve a particular rate of cooling. Fluid reservoir 3530 may be, for example, an IV bag retaining saline (or other suitable conductive cooling fluid) therein, or any other suitable fluid reservoir, such as those detailed above.

Referring still to FIG. 11, in use, as noted above, the determined impedance of the conductive cooling fluid between locations "A" and "B" can provide an indication of various events during use. For example, prior to cooling, system 3010 is primed by pump assembly 3520 operating to pump conductive cooling fluid to fill flowpath 3600 and remove any air bubbles from flowpath 3600. The impedance measurement can be used to determine whether system 3010 has been properly primed, with all air bubbles removed. Specifically, this can be determined by comparing a target "PRIMED" impedance (which may be stored in a memory of controller 3540), representing the impedance in a condition where the cooling fluid flowpath 3600 is full, to the measured impedance between locations "A" and "B." If there is a mismatch, difference outside an acceptable range of variability, or no impedance reading at all, this could indicate that system 3010 has not been properly primed or that priming is not yet complete. In response, pump assembly 3520 may be further operated to pump the conductive cooling fluid through flowpath 3600 to fill flowpath 3600 and remove the air bubbles therefrom. Upon determining that the target "PRIMED" impedance has been achieved (or the measured impedance is within the acceptable range of variability), the pump assembly 3520 may be shut "OFF" and an indication provided that system 3010 is primed and ready for cooling.

In the same manner as above, the impedance measurement can be used to indicate whether there is an obstruction or leakage in the flowpath 3600 and/or whether the surgical instrument is mechanically damaged, as such would result in a different impedance as compared to a corresponding target impedance, an impedance outside the acceptable range of variability as compared to a corresponding target impedance, or a "short circuit" condition, wherein an impedance measurement between locations "A" and "B" is unable to be obtained due to the lack of conductive cooling fluid extending therebetween. Based upon the impedance measurement and comparison, suitable indications may be provided to alert the user that there is an error or that an event that has occurred.

As another example, the impedance measurement may be utilized to determine a cooled state, initiate cooling, deactivate cooling, control cooling, and/or whether cooling is operating properly. This is because the impedance of the conductive cooling fluid will vary depending upon temperature. Thus, for example, controller 3540 can signal pump assembly 3520 to begin pumping the conductive cooling fluid when a target "ON" impedance or impedance within a particular range has been reached and/or to stop pumping the conductive cooling fluid when a target "OFF" impedance or impedance within a particular range has been reached. Delays may also be built-in, for example, where pump assembly 3520 is turned "OFF" a pre-determined time after the target "OFF" impedance or impedance within a particular range has been reached. Controller 3540 may further direct pump assembly 3520 to increase or decrease the flow rate of the conductive cooling fluid, for example, based upon an initial impedance at the beginning of cooling (indicative of the initial temperature), a rate of change in impedance during cooling (indicative of the efficiency of cooling), reaching certain intermediate impedance targets (indicative of the efficiency of cooling), etc. A failure to cool or inefficient cooling can also be detected based upon the impedance, indicating a lack of cooling or an unacceptable slow cooling.

The impedance-based feedback and control detailed above with respect to surgical system 3010 may be used in conjunction with or in place of the other controls detailed hereinabove.

Referring to FIG. 11, in conjunction with FIGS. 1, 5, and 6, as noted above, instruments 100, 1100, 2100 include activation buttons 140, 1140, 2140 that are each selectively activatable in a first position and a second position to supply electrical energy to operate the instrument 100, 1100, 2100 in a low-power mode of operation and a high-power mode of operation, respectively. Such activation buttons 140, 1140, 2140, more specifically, are each coupled to corresponding circuitry that provide low-voltage activation signals in either a first state, indicating the low-power mode of operation, or a second state, indicating the high-power mode of operation, such that the appropriate amount of energy is supplied to operate the instrument 100, 1100, 2100 in the selected mode.

Surgical instrument 3100 may include a similar activation button 3140 as detailed above with respect to instruments 100, 1100, 2100, so as to provide either a "low" or "high" power signal to generator 3510 (or other suitable component such as, for example, a battery that powers generator 3510) to activate surgical instrument 3100 in the corresponding mode. In such a configuration, the electrodes 3514, 3516 utilized to determine impedance, rather than being directly coupled to generator 3510 (or the other suitable component), may be coupled to the circuitry of activation button 3140 and utilize the connections between activation button 3140 and generator 3510 (or the other suitable component), to provide the electrical property measurements to generator 3510 (or the other suitable component) without the need for additional wiring extending between instrument 3100 and cooling module 3500 (or between the electrodes and the battery or generator, when instrument 3100 employs an on-board battery and generator). As the "low" and "high" activation commands provided by activation button 3140 are at least an order of magnitude different from the electrical property signals sensed by electrodes 3514, 3516 to determine impedance, utilizing the same connections does not interfere with the determination of whether activation button 3140 has been activated in either the "low" or "high" power modes.

While several embodiments of the disclosure have been shown in the drawings and described hereinabove, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for cooling a surgical instrument, comprising:
    detecting an electrical property of a conductive cooling fluid at a first position along a closed loop path, wherein the conductive cooling fluid cools a surgical instrument by flowing through the closed loop path from a fluid reservoir in a cooling module, into an input of a surgical instrument, through at least a portion of the surgical instrument, out an output of the surgical instrument, and back to the fluid reservoir, wherein the first position is disposed within or directly adjacent the cooling module;
    detecting an electrical property of the conductive cooling fluid at a second position along the closed loop path, wherein the second position is disposed within or directly adjacent an end effector of the surgical instrument; and
    determining an impedance of the conductive cooling fluid between the first and second positions based upon the detected electrical properties at the first and second positions.

2. The method according to claim 1, further comprising determining whether the closed loop path has been properly primed with the conductive cooling fluid based upon the determined impedance.

3. The method according to claim 1, further comprising at least one of initiating or stopping flow of the conductive fluid along the closed loop path based upon the determined impedance.

4. The method according to claim 1, further comprising determining at least one of air bubbles, a blockage, or mechanical damage to the surgical instrument based upon the determined impedance.

5. The method according to claim 1, wherein the closed loop path extends partially through a blade of an ultrasonic waveguide of the surgical instrument.

6. The method according to claim 1, further comprising: supplying energy to the surgical instrument.

7. The method according to claim 1, wherein the first position is disposed adjacent a distal end of the surgical instrument.

8. The method according to claim 7, wherein the second position is disposed adjacent a cooling module, which includes the fluid reservoir to retain the conductive cooling fluid.

9. The method according to claim 1, further comprising:
    controlling a pump assembly, which is operably coupled to the fluid reservoir and configured to pump the conductive cooling fluid along the closed loop path, based on the determined impedance.

* * * * *